United States Patent [19]
Pfoff

[11] Patent Number: 4,816,031
[45] Date of Patent: Mar. 28, 1989

[54] INTRAOCULAR LENS SYSTEM
[76] Inventor: David S. Pfoff, 950 E. Harvard Ave., 190 350, Denver, Colo. 80210
[21] Appl. No.: 150,042
[22] Filed: Jan. 29, 1988
[51] Int. Cl.$^4$ .............................................. A61F 2/16
[52] U.S. Cl. ........................................................ 623/6
[58] Field of Search ............................................ 623/6
[56] References Cited

U.S. PATENT DOCUMENTS

| | | | |
|---|---|---|---|
| 4,253,199 | 3/1981 | Banho | 623/6 |
| 4,373,218 | 2/1983 | Schachan | 623/6 |
| 4,435,856 | 3/1984 | L'Esperance | 623/6 |
| 4,512,040 | 4/1985 | McClove | 623/6 |
| 4,585,457 | 4/1986 | Kalb | 623/6 |
| 4,619,662 | 10/1986 | Juergens | 623/6 |
| 4,709,996 | 12/1987 | Michelson | 623/6 |

FOREIGN PATENT DOCUMENTS 0162573 11/1985 European Pat. Off. ............... 623/6

OTHER PUBLICATIONS

"Silicon Micromechanical Devices", *Scientific American*, Apr. 1983, pp. 44–55, Angell et al.

Primary Examiner—Richard J. Apley
Assistant Examiner—James Prizant
Attorney, Agent, or Firm—Hugh D. Jaeger

[57] ABSTRACT

An intraocular lens including a PMMA intraocular lens implant, a second soft and pliable lens disposed thereover such as that of silicon, and electromechanical circuitry for regulating the distance between the soft silicon lens and the hard PMMA lens. The electromechanical circuitry can include a microsolar power cell, a microprocessor, a microfluid pump, a micro reservoir for fluid, and a micro DC storage cell. The electromechanical circuitry provides for adjustment of the focal point of the lens system for accommodation from distance to near vision.

13 Claims, 13 Drawing Sheets

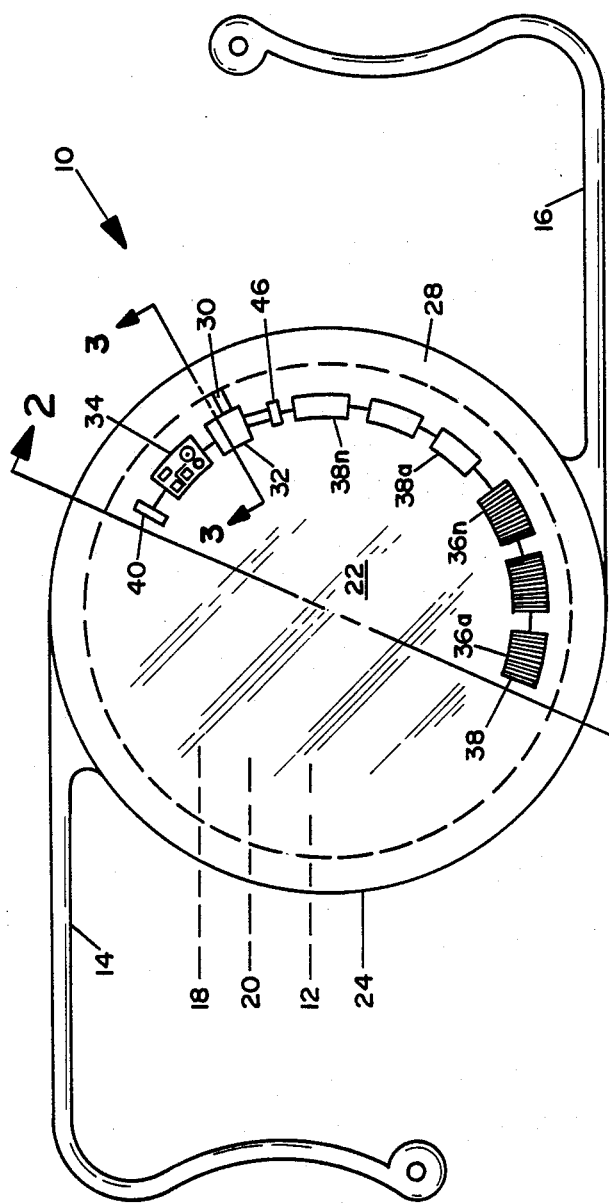
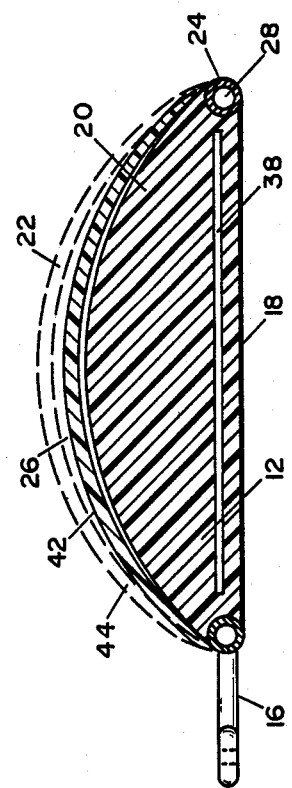

1

INTRAOCULAR LENS SYSTEM

BACKGROUND OF THE INVENTION

1. Field of the Invention

The present invention pertains to an intraocular lens system for implantation after surgery, and more particularly, pertains to an intraocular lens including a hard lens implant, a soft lens over the hard lens and secured thereto, and electromechanical circuitry secured therebetween for adjusting the soft lens over the hard lens.

2. Description of the Prior Art

The currently accepted practice of implantation of intraocular lenses is to replace a normal crystalline human lens of the eye removed at the time of surgery, such as in cataract surgery, with implantation of an intraocular lens such as an anterior chamber lens or posterior chamber lens of PMMA (polymethylmethacrylate). A particular disadvantage of implanting of intraocular lenses is that even with the best medical techniques and sophisticated optical instruments available, the power of the lens implant is not totally accurate for an individual still requiring corrective lenses such as contacts or glasses. Ophthalmologists have never been able to correctly predict for the accommodation of vision from distance to near vision.

The present invention provides for an intraocular lens system including a hard IOL for either the anterior chamber or the posterior chamber, a soft lens disposed thereover, and an electromechanical circuitry disposed therebetween for adjustment of the soft lens with respect to the hard lens through electromechanical circuitry.

SUMMARY OF THE INVENTION

The general purpose of the present invention is to provide an intraocular lens system with a first optical polymethylmethacrylate (PMMA) based in normal hard intraocular lens implant; a second investing coat of a softer but stable plastic, such as hydroxyethylmethacrylate or silicon, which secures the outer perimetry circumference of the first normal hard lens and covers the anterior surface or posterior surface of the hard lens; and an electromechanical circuitry including a storage cell, a microprocessor, a pump, a reservoir for the pump where the intraocular lens system can be fine tuned, in that once the lens is implanted, the electromechanical system can vary the distance between the soft lens and the hard lens allowing for accommodation from distance to near vision.

According to one embodiment of the present invention, there is provided an intraocular lens system including a first optical PMMA based hard normal intraocular lens implant, a second investing coat of stable soft plastic such as silicon secured to and surrounding either the anterior surface or the posterior surface or both of the first lens, and an electromechanical circuitry including a storage cell such as a battery, a microprocessor, a microfluid pump, and a reservoir for fluid for and circuitry for activating the microprocessor to pump fluid from the reservoir about the circumference of the hard-soft lens through a hole between the reservoir and the area of the hard and soft lens for varying the distance between the soft lens and the hard lens, changing the focal point of the lens system, thereby accommodating from distance to near vision. The circuitry for activating the system can be through an external source such as to an implantable switch under the skin or through the more commonly known hand-held radio frequency external device.

One significant aspect and feature of the present invention is an intraocular lens system which allows for varying the focal point of the lens to allow for accommodation from distance to near vision.

Another significant aspect and feature of the present invention is an intraocular lens system which is entirely implantable and can be either turned from an external source acting on an internal implantable component such as a switch or can more commonly be energized and tuned through the commonly available radio frequency system such as that utilized in pacemakers and the like.

A further significant aspect and feature of the present invention is an intraocular lens system which is entirely implantable into the eye, and is self-accommodating to external pressures and movement of the eye. The intraocular lens system can even include micro-solar power cells connected to a direct current storage cell within the intraocular lens providing for continuous power as required.

Having thus described embodiments of the present invention, it is a principal object hereof to provide an implantable intraocular lens system.

An object of the present invention is to provide an intraocular lens system including a first hard lens, a second soft lens disposed over the hard lens, and electromechanical circuitry to vary the distance between the second lens and the first lens to change the focal point of the lens device for accommodating from the distance to near vision.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 illustrates a plan view of an intraocular lens system, the present invention:

FIG. 2 illustrates a sectional view taken along line 2—2 of FIG. 1;

DESCRIPTION OF THE PREFERRED EMBODIMENTS

Figure 4:
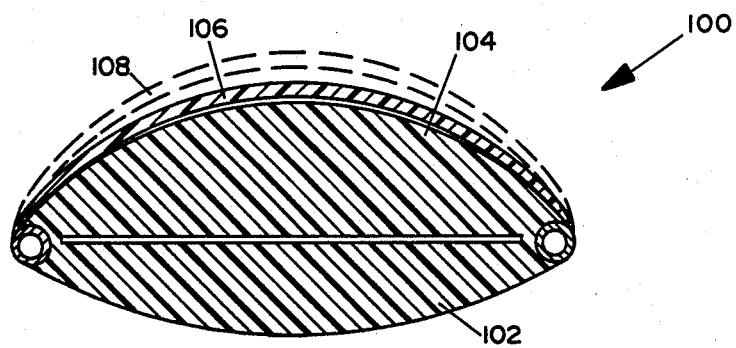
FIG. 4 illustrates an alternative embodiment.

FIG. 1 illustrates a plan view of an intraocular lens system 10, the present invention, including a first optical PMMA based normal hard intraocular lens 12, a plurality of loops 14 and 16 extending therefrom where the lens includes a posterior surface 18 and a convex surface 20. The loops can take any configuration whether the lens be for an anterior chamber or posterior chamber of the eye. The first lens 12 includes a second investing coat of softer but stable plastic such as hydroxyethylmethacrylate or silicone lens 22 which covers the anterior or posterior surface of the first lens 12 and is secured about the circumference 24. A space 26, as illustrated in FIG. 2, provides for fluid, as later described in detail, and for varying the focal point from distance to near vision of the intraocular lens system 10. The second softer, but stable and movable lens 22 secured to the first lens 12 about the circumference 24 provides for the varying of the focal point and accommodating for distance to near vision for fluid pumped therebetween from a reservoir 28 which is disposed about the perimeter of the circumference of the first lens 12, as also illustrated in FIG. 2. The fluid passes from the reservoir 28 through a hole 30 driven by a pump 32 and controlled by a microprocessor 34. A plurality of photovoltaic solar power cells 36a-36n power a plurality of storage batteries 38a-38n for driving a microprocessor circuitry as well as the pump 32. The pump 32, the microprocessor 34 and control circuitry, the solar power cells 36a-36n, and the storage cells 38a-38n are all positioned in the first lens 12 about an inner perimeter 38 as also illustrated in FIG. 2. An implantable switch 40 can connect to the microprocessor control circuitry as later described. In the alternative, an RF loop pickup coil can connect to the microprocessor 34 as later described.

FIG. 2 illustrates a sectional view taken along line 2—2 of FIG. 1, where all numerals correspond to those elements previously described. Particularly, the lens is illustrated in a deactivated position 42 and an activated position 44, as illustrated in dashed lines. In the activated position 44, fluid such as distilled water or the like would be pumped from the reservoir 28 by the pump 32 through the microprocessor 34 to elevate the softer pliable second lens 22 over the first lens 12 as also illustrated in FIG. 1.

Figure 3:
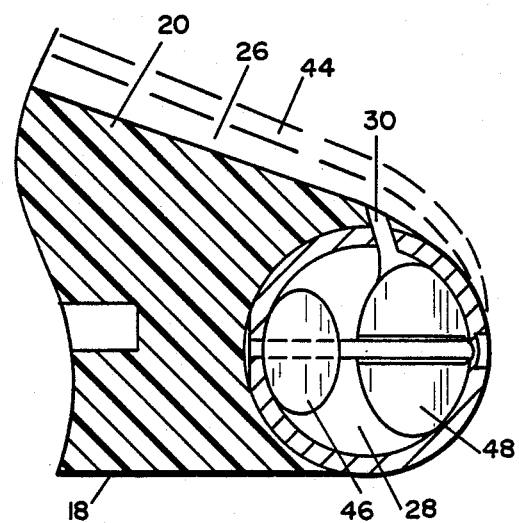
FIG. 3 illustrates a sectional view taken along line 3—3 of FIG. 1.

FIG. 3 illustrates a view taken along line 3—3 of FIG. 1 including all numerals which correspond to those elements previously described. Further, a motor 46 is illustrated which is connected to the microprocessor control circuitry and includes pump paddles 48 for driving fluid through the hole 30 of the reservoir 28.

MODE OF OPERATION

The refractive power of an optical system is based on the surfaces through which the rays of light pass, and the index of refraction materials and the optical materials. The intraocular lens system 10 utilizes the normal optical properties of the conventional hard-plastic PMMA intraocular lens 12 and adds to this by allowing the microprocessor 34, through the pump 32, to fill a fluid reservoir 28 bounded on one refracting surface by the soft second lens membrane 22 and on the other refractive surface by the hard optical PMMA lens 12. The total effect of the intraocular lens system 10 is to increase or decrease the curvature of the soft second lens 22, thereby changing the optical power of the intraocular lens system 10. The lens system can be activated from a hand-held radio frequency control device picked up by a small radio-frequency loop for controlling the microprocessor 34, as is commonly done with pacemaker systems. Power to drive the system comes from the solar-powered charged batteries within the implant or could be generated to the implant by radio frequency currents. The method of fixation of the intraocular lens system 10 is similar to that currently used in intraocular lenses inside either the posterior chamber or the anterior chamber.

ALTERNATIVE EMBODIMENT

FIG. 4 illustrates a cross-sectional view of an alternative embodiment of the present invention of an implantable intraocular lens system 100, including a minus lens 102 located in the anterior chamber and a plus lens 104 positioned in the capsular bag, both under the control of a microprocessor control circuitry with respect to a pliable lens 106 providing for zoom effects, thereby creating a telescopic lens system. The pliable lens 106 is illustrated in dashed lines 108 when in a raised position through fluid between the lenses as previously described.

FIGS. 5-14 illustrate a variety of pumps which may be used in this invention. Such pumps can be fabricated by using techniques similar to those described in a paper "Silicon Mechanical Devices" by James B. Angell, Stephen C. Terry and Phillip W. Barth, published in the *Scientific American,* April, 1983.

One embodiment of the pump, fabricated on a silicon substrate, has a first input valve and a second output valve with a communicating pump chamber having a diaphragm at one side. The diaphragm is sufficiently thin to allow flexing either by means of electromagnetic fields induced with windings on the diaphragm and a base member, or by electrostatic forces resulting from charges applied to closely spaced plates on the diaphragm and the base member. The input and output valves may be of the ball-check type in which a circular ball is disposed within a valve chamber. The ball may be coated with a conductive material to allow it to be moved with electromagnetic or electrostatic forces. Instead of ball-check valves, diaphragm valves can be used, by creating an extension of the pump diaphragm or by fabricating discrete diaphragms for each valve.

Alternatively, the diaphragm may have an elongated instead of circular shape. In such an embodiment, the windings or plates are arranged to allow the diaphragm to be deflected to produce a wave, or peristaltic action on the fluid. This configuration has the advantage of being capable of operation without the use of check valves at the inlet and outlet ports. Since this version has no free moving parts and crystalling silicon does not suffer from fatigue, the mechanical life of such a pump is virtually infinite.

The selection of the embodiment will be dependent on the volume of fluid to be pumped, the viscosity of the fluid, the pressure required, the nature of the reservoir, the available power, the size and geometry of the space available on the silicon substrate and the length of time the device is to operate within the eye without failure or maintenance.

Figure 5:
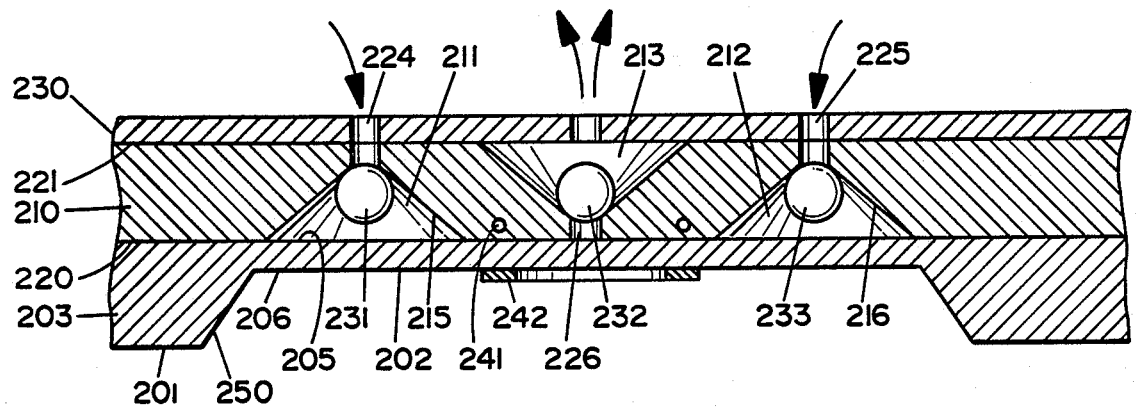
FIG. 5 illustrates a partial cross-sectional view taken along the line 5—5 of FIG. 6, showing a diaphragm pump according to the invention having ball-check valves at the inlet and outlet ports.

With reference to FIG. 5, a base member 201 of single crystal silicon or like material, having had the characteristic that the etching rate may be altered by doping, has an extremely thin diaphragm portion 202 and a peripheral portion 203. The diaphragm portion is fabricated from a silicon wafer by an anisotropic etching process in accordance with known micromachining techniques such as described in the above mentioned paper. The silicon wafer is doped on one side with boron to a depth determined by the desired thickness of the diaphragm. The doping is made on the side 205, opposite the side 206 from which etching will occur. The doping is done to slow the etching process in the doped region. It has been found that anisotropic etchants, such as aqueous sodium hydroxide, aqueous potassium hydroxide, or the mixture known as EDP will not only etch in a fashion dependent on the orientation of the atomic planes of the silicon wafer, thereby avoiding the undercutting of the etch resist which results when isotropic etchants are used, but it also etches at a rate which is dependent on the doping (level of impurities) in the material. The etching action of potassium hydroxide and EDP on silicon that is heavily doped with boron is much slower than undoped silicon or silicon that is lightly doped with boron.

Thus, etching a wafer from a side which is not doped with boron, in the direction of the side heavily doped with boron to a depth of the desired diaphragm thickness, proceeds rapidly through the wafer until the doped region is reached. The etching process slows to a virtual stop, allowing great latitude in the timing of the etch without substantially affecting the ultimate thickness of the diaphragm.

It is even possible to develop diaphragms which are not coplanar with the rest of the wafer by growing an additional layer of exitaxial silicon over the surface of the silicon crystal after the doped layer is formed. This would allow the diaphragm to define a surface of a cavity between the diaphragm and the abutting cover member.

If any holes are to be later produced in the diaphragm, they will be masked off to prevent doping from occurring. An oxide coating is developed on the surface of the wafer and a coating of photoresist is applied to the oxide. A photographic mask which carries the pattern of the diaphragm is placed in contact with the photoresist and the wafer exposed to ultraviolet radiation. Then the wafer is rinsed in a developing solution which removes the exposed photoresist. The wafer is then placed in a bath of hydrofluoric acid which removes the oxide coating in the exposed areas to reveal the underlying silicon wafer. The remaining photoresist is then removed with hot sulfuric acid or similar solution, leaving a clean silicon wafer with portions masked by the oxide layer.

The etching process proceeds with an anisotropic etchant for a period of time sufficient to ensure that the undoped silicon is removed to the depth of the desired diaphragm thickness.

The valve plate 210 is also fabricated from crystalline silicon or like material using anisotropic etching processes to produce tapered walls in the valve ports. The inlet valves 211 and 212 have conical or pyramidal sloping walls 215 and 216 respectively. These walls are formed by anisotropic etching through holes in a mask on the surface 220 of the valve plate 210 and slope at an angle dependent on the crystal orientation of the valve plate 210. If the (100) surface is etched, the angle of the walls with respect to the surface will be 55 degrees. While it would be possible to simply continue the etching process from the surface 220 until the opposite side 221 was reached, the size of the resulting hole in side 221 would be dependent on the etch rate, making it difficult to accurately control. It is preferable to heavily dope the side 221 with boron in all areas except those which are to be etched. Thus, when the anisotropic etch reaches the area of doping which surrounds ports 224 and 225, the etch continues in a relatively straight line, consuming only the undoped portion which defines the holes.

The outlet valve 213 is fabricated by the same process, that is, the region of port 226 is left undoped to provide a rapid etch when reached by the anisotropic etchant proceeding from side 221.

A valve cover plate 230 which may be silicon, glass or other suitable material is provided with holes which line up with the ports 224 and 225 of valve plate 210.

Assembly of the base member 201 with the valve plate 210 can be accomplished with conventional semiconductor bonding techniques. It is important only that the diaphragm portion 202 not be bonded to the valve plate 210, leaving the diaphragm free to be deflected away from the valve plate.

The valve cover plate 230 can be bonded to the valve plate 210 with conventional techniques. In the event that the valve cover plate is made of glass, the bonding may be accomplished by anodic bonding which is a well known electrostatic process sometimes called the Mallory process since it was developed by George Wallis and Daniel Pomerantz of the Mallory company.

Prior to bonding the base member, the valve plate and the valve cover, it is necessary to insert the balls 231, 232 and 233 into position. Depending on the particular application of the pump, it may or may not be necessary to bias the balls against their respective valve seats. In some applications, the liquid flow through the valves induced by diaphragm movement may be sufficient to provide satisfactory valve action. If this is not adequate, the balls may be coated with conductive material such as gold, and suitable conductive regions may be provided in the sloping walls 215 and 216 of the valves. When these regions are electrically charged, the resulting electrostatic forces will be effective to attract or repel the balls. Since the normal fluid flow will be in the direction assisting the electrostatic force, very little additional force is required.

Alternatively, the balls may be biased with electromagnetic force provided by a winding made by a conductor in the region of the valve walls. Such a conductor could take the form of a diffused winding in the surface of the walls. The magnetic field resulting from current flow through the winding would induce a current in the conductive coating of the balls, causing the balls to move away from the winding.

The diaphragm motion is produced by a pair of windings 241 and 242, located on the valve plate 210 and diaphragm portion 202, respectively. When electrical current is passed through these windings 241 and 242 to produce similarly poled electromagnetic fields, the resulting mechanical force pushes the diaphragm portion 202 away from the valve plate 210. The displacement of diaphragm portion 202 away from the valve plate 210 causes fluid to be drawn through the inlet valves 211 and 212 into the region between the diaphragm portion 201 and the valve plate 210. At the same time, it may be desirable to energize the plates or windings associated with the inlet valves 211 and 212 to ensure that they are open and the winding or plate associated with outlet valve 213 to ensure that it remains closed.

When the diaphragm portion 202 has reached the point of maximum deflection, and the resulting pump chamber has filled with fluid, the signals to inlet valves 211 and 212 and outlet valve 213 are reversed and the drive to the diaphragm windings 241 and 242 is either terminated or reversed, causing diaphragm portion 202 to revert to its normal, undeflected, position. The fluid previously drawn into the pump cavity is then expelled through the outlet valve 213. Again, the preponderant portion of the energy required to operate the valves will be supplied by fluid flow.

Figure 6:
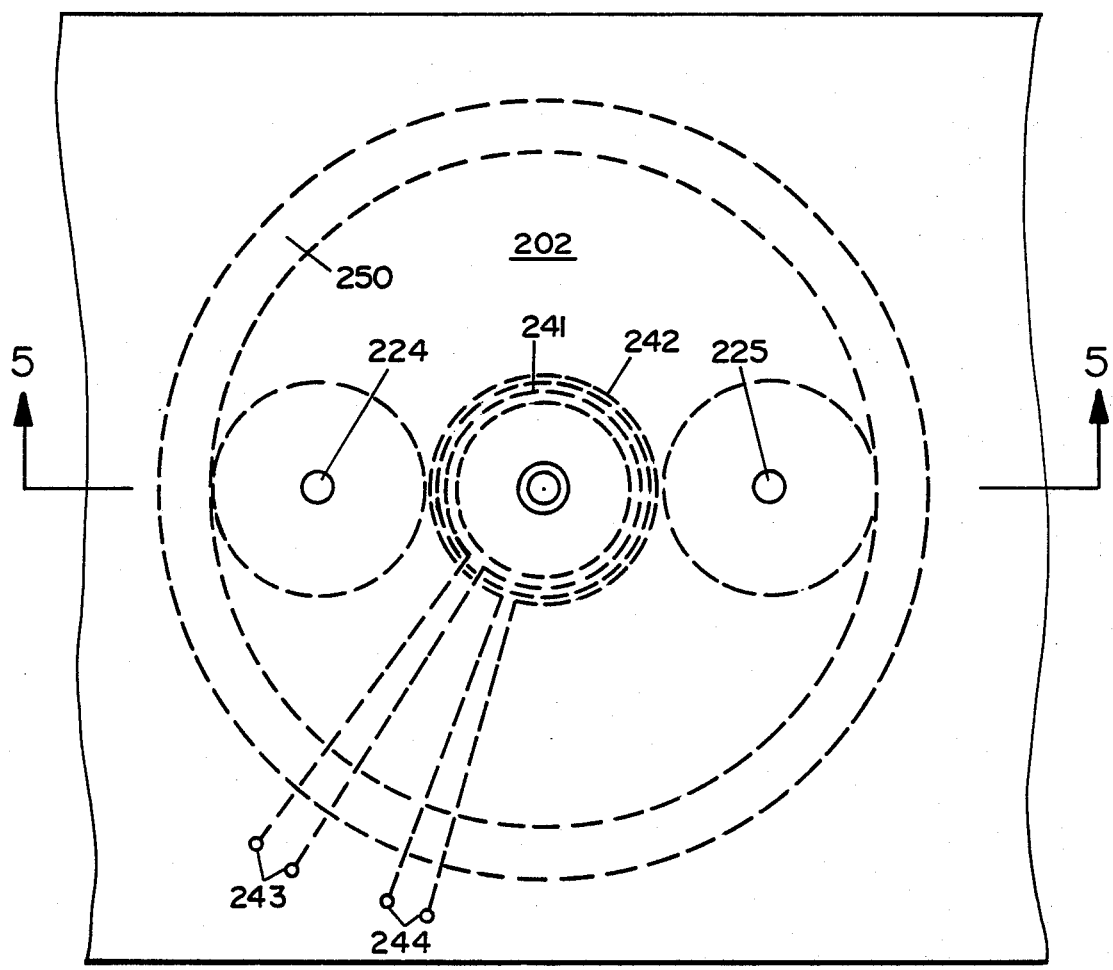
FIG. 6 illustrates a top view of the diaphragm pump shown in FIG. 5.

With reference to FIG. 6, which shows a top view of the pump of FIG. 5, the diaphragm portion 202 abuts angled side wall 250, which extends downwardly from side 206 at a 55 degree angle. Ports 224 and 225 are located near the periphery of diaphragm portion 202. The central portion of diaphragm portion 202 carries a diaphragm winding 242, and the central portion of valve plate 210 includes an winding 242. Terminals 243 and 244 connect to windings 241 and 242, respectively. When energized by oppositely poled currents, the windings attract each other and cause the diaphragm portion 202 to be drawn against the valve plate 210. When similarly energized, the windings repel each other and cause the diaphragm portion 202 to move away from valve plate 210.

It can be seen that the failure of any of the valves to operate properly does not result in leakage through the pump since the deenergized diaphragm seals the opening into the outlet valve. The "real estate" on the silicon wafer required for the pump is only a small portion of that available on such wafers, and the wafer can therefore be shared with conventional semiconductor devices such as transistors, diodes, photoelectric sensors, solar cells, radio frequency sensors, pressure sensors, microprocessors and data storage devices as shown in FIG. 1.

The terminals 243 and 244 may be directly connected to drive circuits energized in accordance with signals from a microprocessor. The microprocessor then operates under the control of a stored program which is modifiable by means of data entered via photo sensors or radio frequency sensors. This would enable the operation of the pump to be modified without direct physical connection to the pump, a prime requirement for a device which could be implanted deep within the human body or other inaccessible location.

Figure 7:
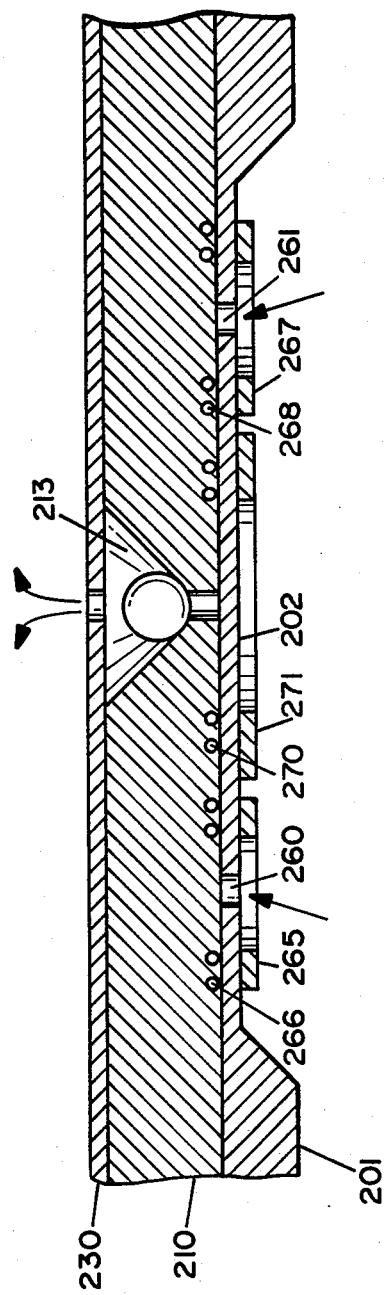
FIG. 7 illustrates a partial cross-sectional view taken along line 7—7 of FIG. 8, showing a diaphragm pump according to the invention having diaphragm valves at the inlet and a ball-check valve at the outlet port.
Figure 8:
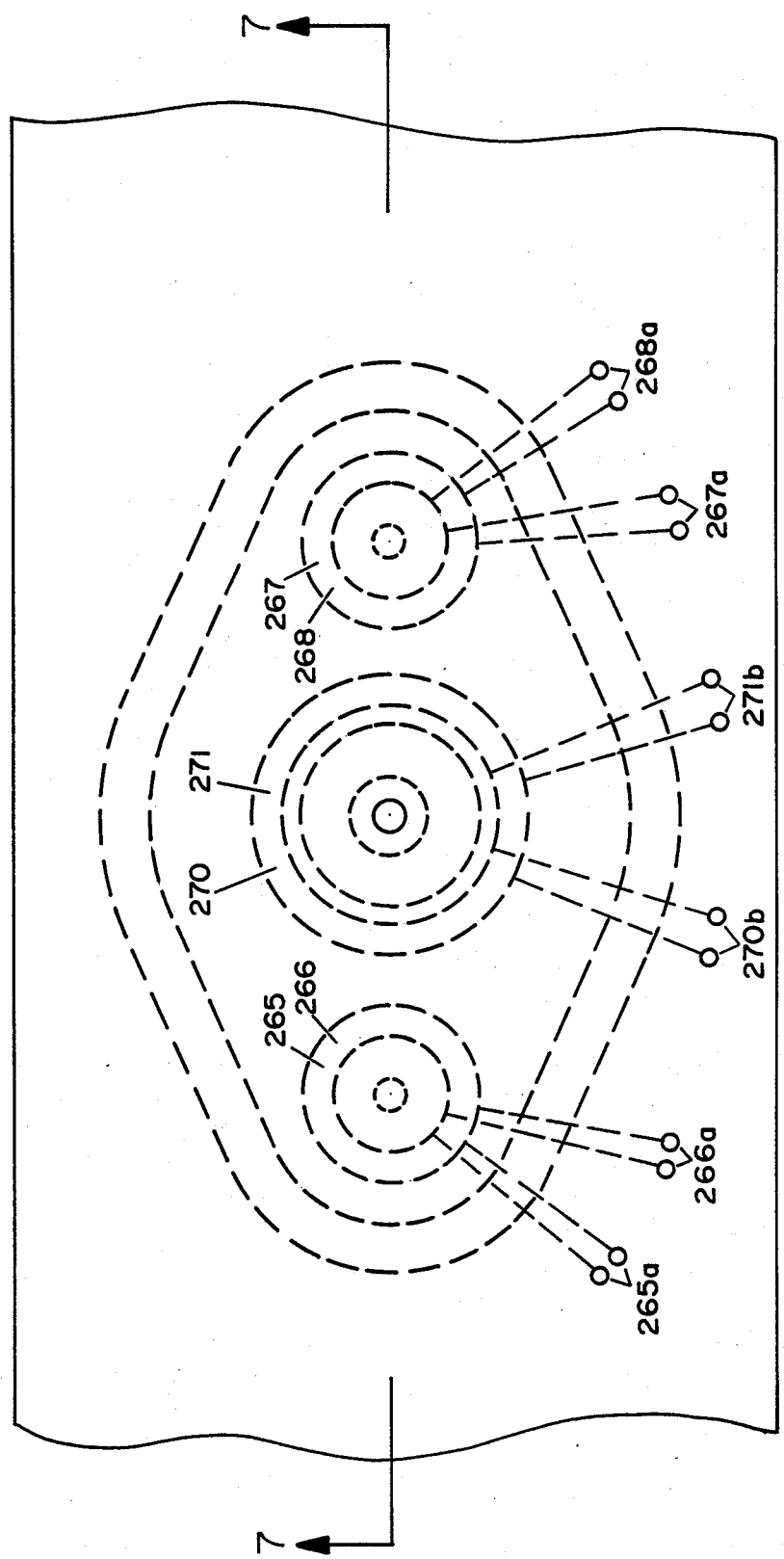
FIG. 8 illustrates a top view of the diaphragm pump shown in FIG. 7.

The embodiment shown in FIGS. 7 and 8 is similar to that of the FIGS. 5 and 6 except that diaphragm valves are used at the inlet instead of ball check valves. This embodiment has the advantage of fewer mechanically free parts, and therefore, should be less likely to fail. It also retains the advantage of being fail-safe, in that failure of the pump does not result in leakage between the inlet and outlet.

The diaphragm portion 202, having an elongated or generally oval shape, is fabricated in the same fashion as previously described, except that two or more inlet ports 260 and 261 are etched near the periphery of the diaphragm in the end regions thereof. Each inlet port has associated pairs of actuator windings 265, 266, 267, 268, respectively. Windings 265 and 267 are affixed to the diaphragm while windings 266 and 268 are within valve plate 210. When energized with the appropriately poled currents, the windings operate to either repel the portion of diaphragm portion 202, adjacent inlet ports 260 and 261, from the valve plate 210 or to attract it thereto. Thus, the region of diaphragm portion 202 which lies adjacent to the inlet ports 260 and 261 operates as a valve to either allow flow of fluid through inlet ports 260 and 261 when that region of the diaphragm is spaced from the valve plate 210 or to prevent such flow when the region lies against the valve plate 210. It will be appreciated that the diaphragm portion 202 is sufficiently thin to allow the individual regions to flex without causing corresponding movement in other spaced regions.

In operation, the actuator windings 265-268, associated with the inlet ports 260 and 261, are first energized by signals applied to terminals 265a-268a, respectively, to open the ports. Subsequently, the actuator windings 270 and 271 are energized by signals applied to terminals 270b and 271b to cause the central portion of diaphragm portion 202 to move away from valve plate 210. The movement of diaphragm portion 202 away from valve plate 210 causes fluid to be drawn through inlet ports 260 and 261 into the pump chamber.

After a short period of time, to allow the pump chamber to fill with fluid, the actuator windings 265-268 are deenergized, allowing the diaphragm in the region of inlet ports to relax and close these ports. When the inlet ports are closed, the actuator windings 270 and 271 are deenergized, or the flow of current in one winding reversed, causing the central portion of diaphragm portion 202 to move against the adjacent portion of valve plate 210. This causes the fluid in the pump chamber between valve plate 210 and diaphragm portion 202 to be expelled through the outlet valve 213. The cycle is then repeated.

Figure 9:
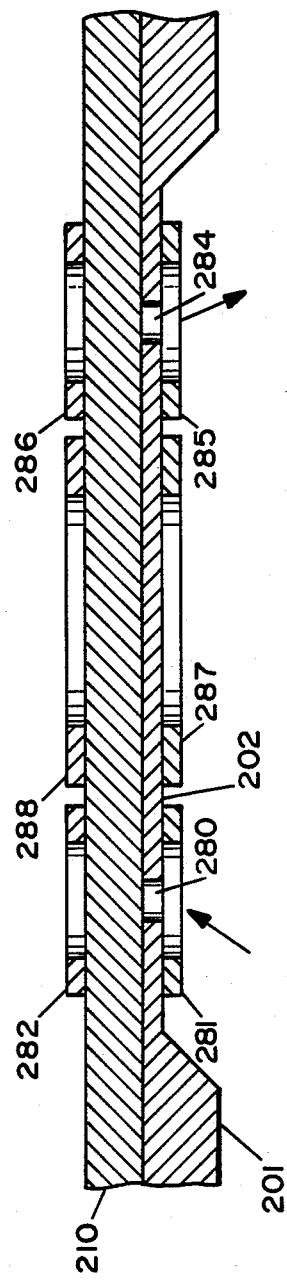
FIG. 9 illustrates a partial cross-sectional view taken along lines 9—9 of FIG. 10, showing a diaphragm pump according to the invention having diaphragm valves at the inlet and outlet ports.
Figure 10:
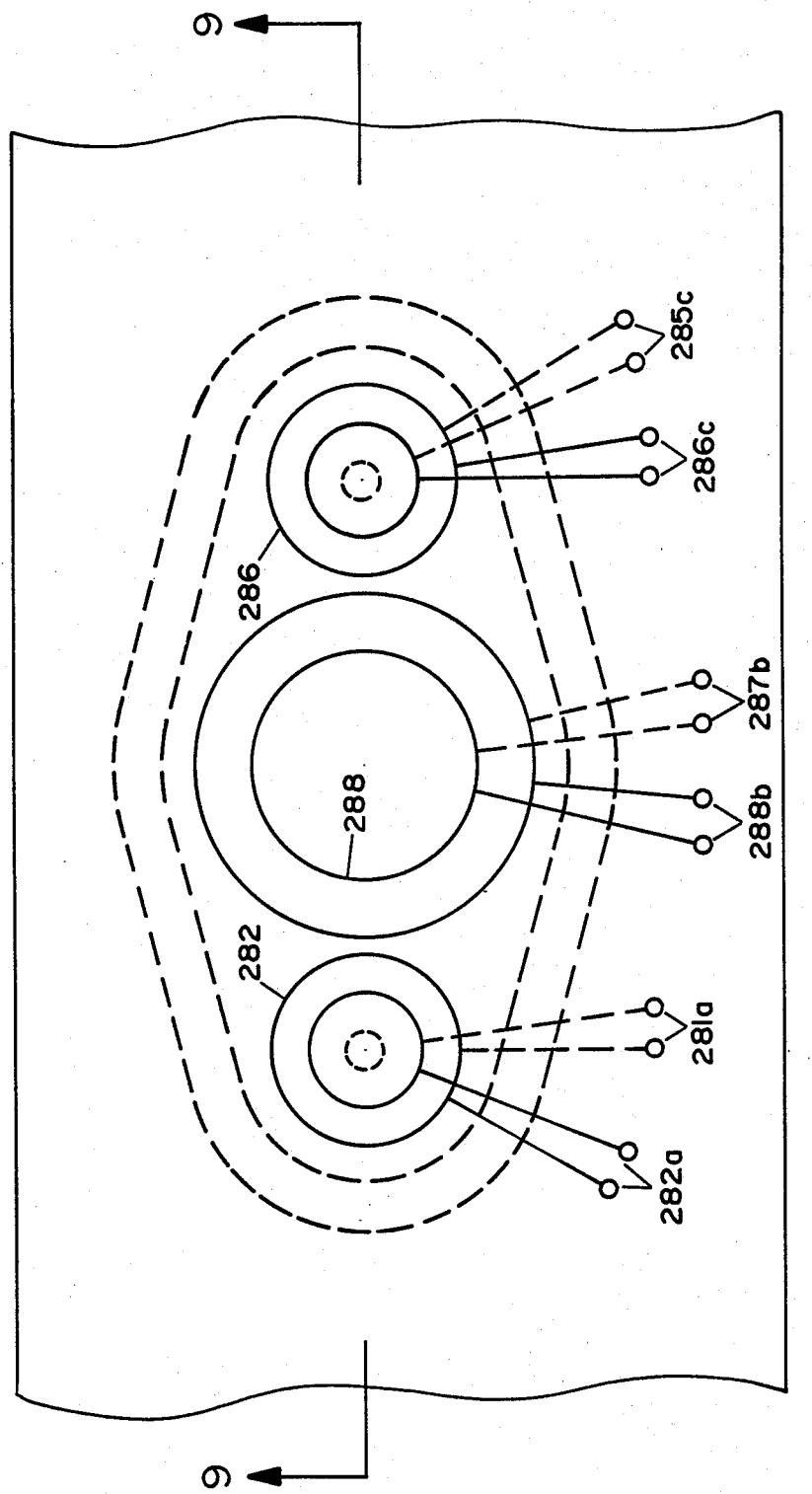
FIG. 10 illustrates a top view of the diaphragm pump of FIG. 9.

The embodiment of FIGS. 9 and 10 uses diaphragm valves at both the inlet and outlet ports, thereby avoiding the need for any free moving mechanical parts such as the balls in the check valves of the earlier described embodiments. The base member 201 has an etched diaphragm portion 202, which can be fabricated as earlier described. The diaphragm has an inlet port 280, having associated diaphragm valve actuator winding 281, mounted on the diaphragm, and actuator winding 282, mounted on the valve plate 210. Energization of windings 281 and 282 with the appropriately poled signals causes motion of the diaphragm in the region of inlet port 280. Signals of one polarity cause the diaphragm to move away from valve plate 210 and open inlet port 280, and signals of the opposite polarity cause motion of the diaphragm toward the valve plate 210 to close inlet port 280, thereby providing the necessary inlet valve action.

Diaphragm portion 202 also has an outlet port 284, having associated diaphragm valve actuator winding 285, mounted on the diaphragm, and actuator winding 286, mounted on the valve plate 210. Energization of these windings with the appropriately poled signals causes the diaphragm in the region of outlet port 284 to move away from valve plate 210 and open outlet port 284, and signals of the opposite polarity cause motion of the diaphragm toward valve plate 210 to close outlet port 284, to provide the necessary outlet valve action for the pump.

A pair of pump diaphragm actuator windings, winding 287, mounted on diaphragm portion 202, and winding 288, mounted on valve plate 210, serve to move the central portion of the diaphragm for pumping action.

In operation, appropriately poled signals are first applied to input terminals 281a and 282a of inlet valve actuator windings 281 and 282, respectively, to move the portion of diaphragm portion 202 in the region of inlet port 280 away from valve plate 210 and open the inlet valve and allow fluid to flow into the pump chamber through inlet port 280. At the same time or shortly thereafter, appropriately poled signals are applied to input terminals 287b and 288b of actuator windings 287 and 288, respectively, to cause the central portion of diaphragm portion 202 to move away from valve plate 210 and draw fluid through inlet port 280 into the pump chamber between diaphragm portion 202 and valve plate 210. When diaphragm portion 202 is fully distended, the signals applied to one of terminals 281a and 282a are either reversed, driving the portion of diaphragm portion 202 surrounding inlet port 280 toward the valve plate 210, or simply terminated, allowing the diaphragm in the region of inlet port 280 to return to its normal unstressed position adjacent valve plate 210. In either case, the return of diaphragm portion 202 to a position abutting valve plate 210 causes the inlet port 280 to close, trapping the fluid drawn therethrough in the pump chamber.

At this point, an appropriately poled signal is applied to the terminals 285c and 286c of outlet valve actuator windings 285 and 286, respectively, to move the portion of the diaphragm in the region of the outlet port 24 away from valve plate 210 and open the outlet valve and allow the fluid in the pump chamber to flow out. The signals applied to one of terminals 287b and 288b of pump diaphragm actuator windings 287 and 288 are reversed to drive the diaphragm portion 202 toward valve plate 210 or simply terminated, allowing diaphragm portion 202 to return to its normal unstressed position, and, in so doing, expel the previously indrawn fluid through outlet port 284. When the diaphragm portion 202 has reached the position against the valve plate 210, the signals to terminals 285c and 286c are either reversed or terminated to position the portion of the diaphragm portion 202 surrounding outlet port 284 against valve plate 210 and thereby close the outlet valve.

It will be appreciated that the inlet and outlet valves include the portion of the diaphragm which surrounds the respective ports, the actuator windings and the cooperating portion of the valve plate.

Figure 11:
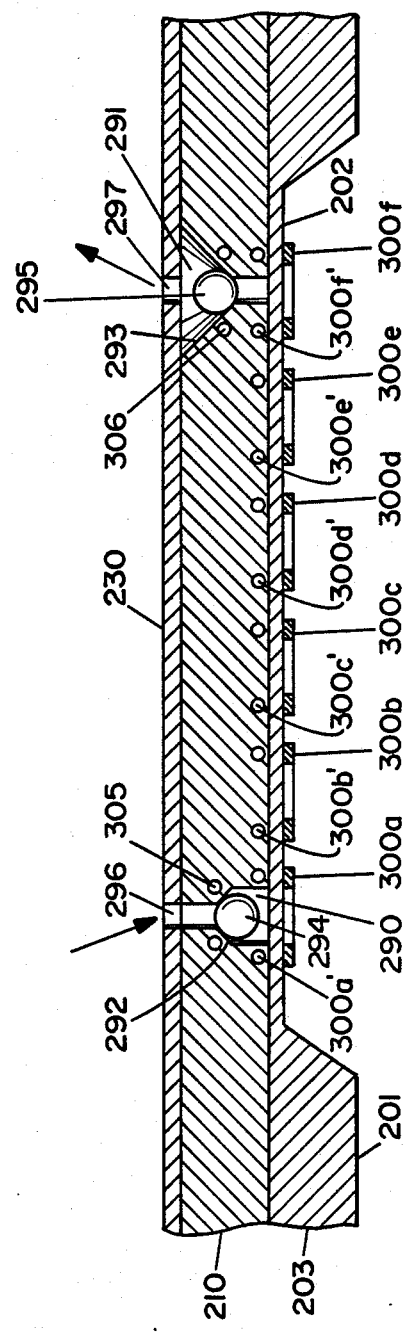
FIG. 11 illustrates a partial cross-sectional view taken along line 11—11 of FIG. 12, showing a peristaltic pump according to the invention having ball-check valves at the inlet and outlet ports.
Figure 12:
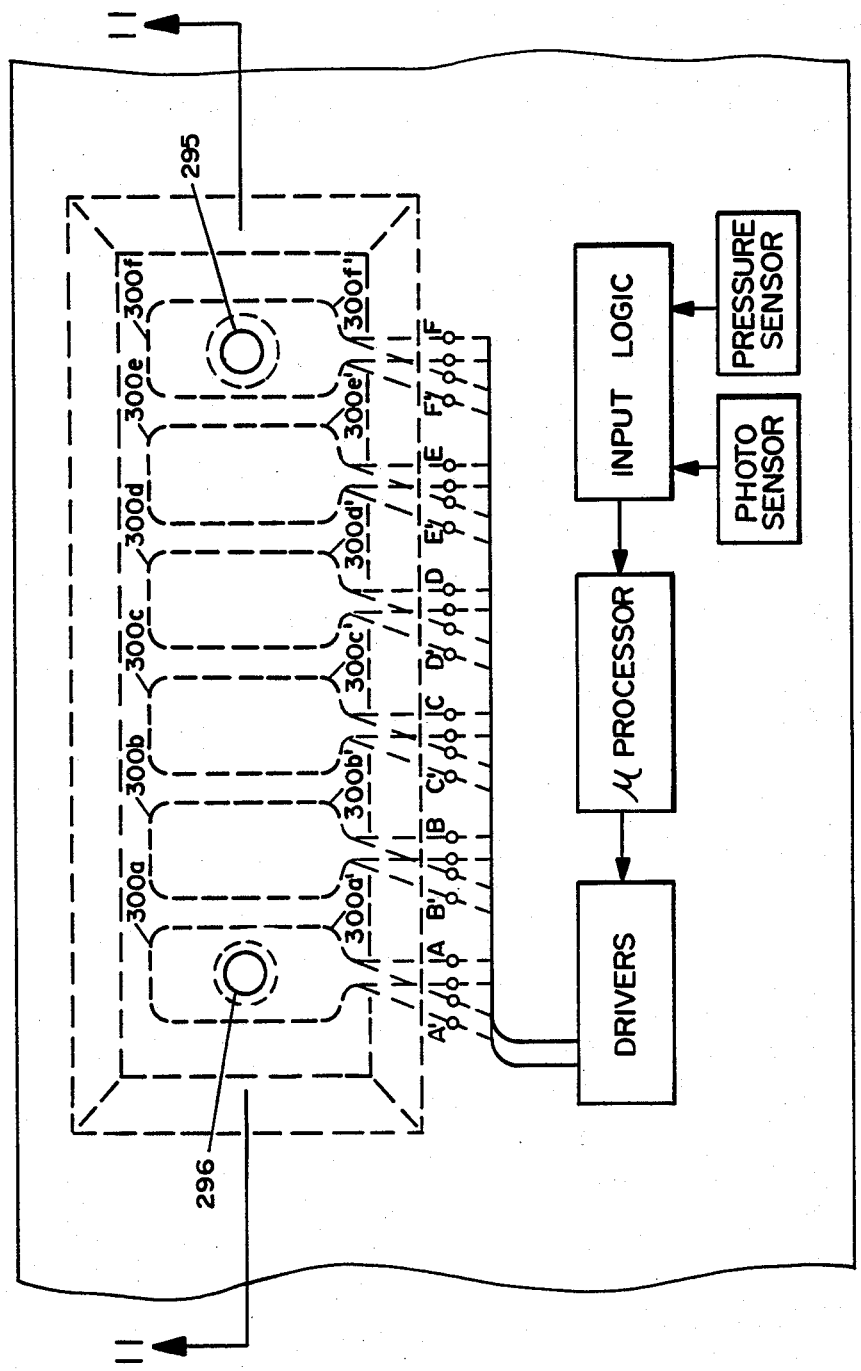
FIG. 12 illustrates a top view of the peristaltic pump of FIG. 11.

The previous embodiments can be characterized as diaphragm pumps. The embodiment of FIGS. 11 and 12 is a peristaltic pump, in which the pumping action is provided by creating a "bulge" in an elongated chamber and moving the bulge from the inlet port to the outlet port. In this invention, although different terms are used to characterize the pumping action, both types utilize an etched, exceptionally thin diaphragm of crystalline silicon as the pumping element.

With specific reference to FIG. 11, a base member 201 of crystalline silicon or like material has an extremely thin diaphragm portion 202 surrounded by a peripheral portion 203. As can be seen from the top view of FIG. 12, the diaphragm has an elongate, generally rectangular shape. The diaphragm lies against the valve plate 210 which contains an inlet valve 290 and an outlet valve 291. Each of the valves 290 and 291 is of the ball-check type having a tapered valve seat 292 and 293, respectively. Ball elements 294 and 295 cooperate with the valve seats 292 and 293 to allow flow only in the inward direction in the case of inlet valve 290 and in the outward direction in the case of outlet valve 291.

The diaphragm portion 202, the valve seats 292 and 293, together with the inlet port 296 and outlet port 297 are fabricated by an anisotropic etch process as previously described. Similarly, the base member 201, the valve plate 210 and the valve plate cover 230 are bonded as previously described, leaving the area between the diaphragm portion 202 and the valve plate 210 unbonded so that the diaphragm is free to move.

A plurality of actuating means comprising pairs of electrical windings 300a—300a', 300b—300b', 300c—300c', 300d—300d', 300e—300e', 300f—300f' are disposed in lengthwise fashion along the diaphragm portion 202. The sequence of windings 300a-300f is mounted on diaphragm portion 202. A corresponding sequence of windings 300a'—300f' is mounted on valve plate 210 in closely spaced opposition to the windings on diaphragm portion 202. The windings on valve plate 210 and diaphragm portion 202 can be in the form of diffusion formed conductors or discrete plating and have terminals A-F and A'-F', respectively, connected to the windings 300a-300f and 300a'-300f' as shown in FIG. 12.

A pair of actuator windings 305 and 306, imbedded in the sloping walls of the valve seats 292 and 29 provide means for controlling the position of the ball elements 294 and 295, respectively. Alternatively, the actuator windings 305 and 306 may be used as plates for the introduction of an electrostatic charge which causes the motion of ball elements 294 and 295.

Operation of the peristaltic version of the pump begins with the opening of inlet port 296 and the movement of the portion of the diaphragm actuated by the windings 300a and 300a'. When the inlet valve is opened and the diaphragm actuated by windings 300a and 300a', the resulting movement of the diaphragm portion 202 away from valve plate 210 causes fluid to be drawn through the inlet port 296 into the pump cavity formed by the displaced diaphragm.

With the inlet port still open and the windings 300a and 300a' still energized, the windings 300b and 300b' are energized to displace the portion of diaphragm portion 202 actuated by these windings. After the portion of diaphragm portion 202 actuated by the windings 300b and 300b' has reached the point of its maximum displacement, the actuating windings 300a and 300a' associated with the diaphragm and actuator winding 305 associated with the inlet port are deenergized, causing the inlet port 296 to close and the portion of the diaphragm portion 202 actuated by the windings 300a and 300a' to move back against the valve plate 210. At the same time, the windings 300c and 300c' are energized.

At this point both the inlet and outlet valves are closed and there is a fluid filled "bulge" in the diaphragm at the point where actuator windings 300b—300b' and 300c—300c' abut. This fluid filled bulge is now moved lengthwise along the diaphragm by subsequent sequential energization of the windings 300d—300d' through 300f—300f'.

Figure 15:
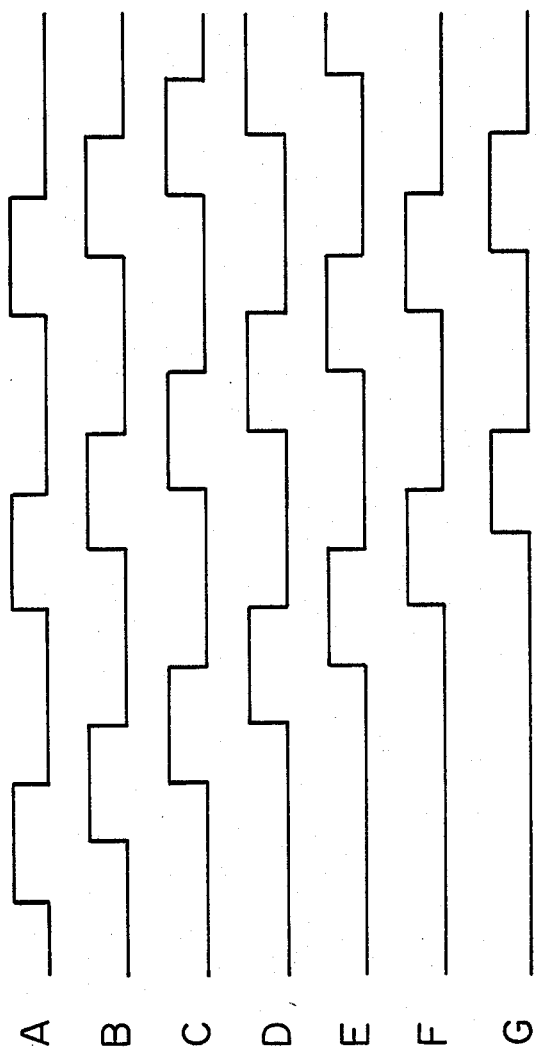
FIG. 15 illustrates a timing diagram showing the wave forms of the signals used to energize the electrical actuators for the pumps of FIGS. 5-14.

FIG. 15 is a timing diagram showing the fashion in which the actuator windings are energized. The inlet valve is energized to be opened at the same time as windings 300a—300a'. The outlet valve is energized to be opened at a time shown in the line G, and closed at a point subsequent to the deenergization of windings 300f and 300f' (the timing line F). The timing line A corresponds to the signal applied to the terminals A and A' associated with windings 300a and 300a'. Similarly, timing line B corresponds to the signal applied to terminals B and B, associated with windings 300b and 300b'.

As shown in FIGS. 1 and 12, the electronic components necessary to develop the drive signals can be fabricated on the same silicon crystal as the pump itself. Such components would include drivers for the individual actuator windings associated with the diaphragm and valves, a microprocessor having data storage capability to store a control program and commands issued from a remote source, photosensors for transmitting information to the microprocessor where the pump is located in a location where light can be used for this purpose, for example, the eye, pressure sensors to determine the output pressure of the pump or the reservoir into which it is pumping and other semiconductor devices.

Figure 13:
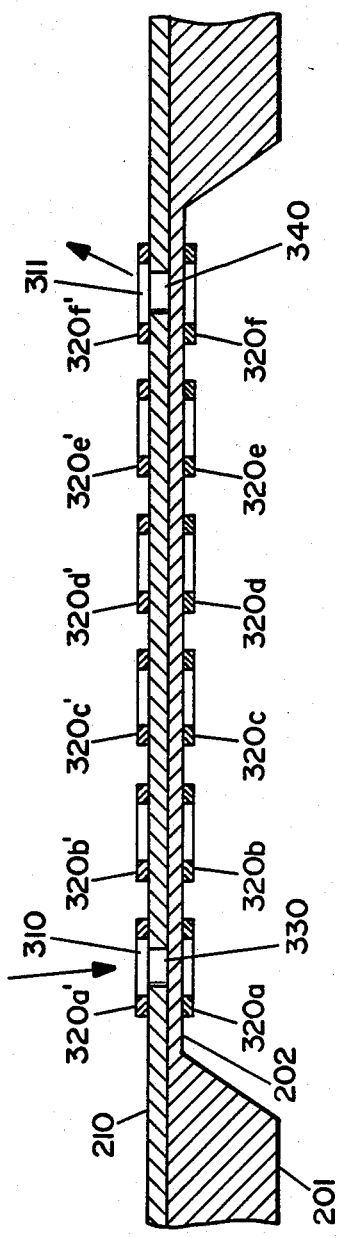
FIG. 13 illustrates a partial cross-sectional view taken along line 13—13 of FIG. 14, showing a peristaltic pump according to the invention having diaphragm valves at the inlet and outlet ports.

FIG. 13 shows a peristaltic pump in which both the inlet valve and the outlet valve are of the diaphragm type. The absece of free moving mechanical parts such as the check-valve balls tends to make the pump more reliable and results in longer life.

Figure 14:
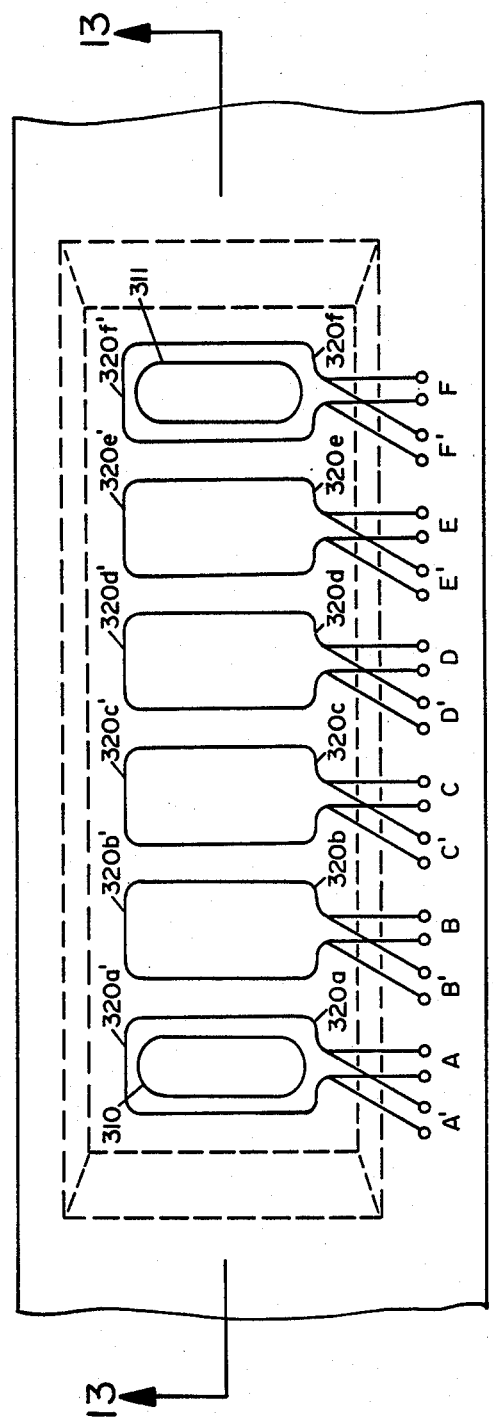
FIG. 14 illustrates a top view of the peristaltic pump of FIG. 13.

The base member 201 has a very thin diaphragm portion 202 which is fabricated by an anisotropic etch process as previously described. The diaphragm portion 202 has an elongate rectangular shape as shown in FIG. 14. A valve plate 210 has an inlet port 310 and an outlet port 311. The valve plate is affixed to the base member through conventional semiconductor techniques, leaving the diaphragm portion 202 unbonded and free to move. Inlet valve actuator winding 320a, mounted on the diaphragm portion 202 and winding 320a', mounted on the valve plate 210, are positioned to move the portion of diaphragm portion 202 which abuts inlet port 310. When these windings are energized with the appropriately poled currents to develop opposing magnetic fields, the diaphragm portion 202 in the vicinity of the inlet port 310 will flex and move away from the valve plate 210, thereby opening the inlet valve 330 comprising the inlet port 310 and the abutting portion of diaphragm 202. When the inlet valve 330 is open, fluid is drawn through inlet port 310 into the pump chamber formed between the displaced diaphragm portion 202 and valve plate 210.

With the windings 320a and 320a' still energized, the windings 320b and 320b' are energized to displace the portion of diaphragm portion 202 actuated by these windings. As this portion of the diaphragm is displaced it enlarges the pump chamber and causes still more fluid to be drawn through inlet port 310 into the pump chamber between diaphragm portion 202 and valve plate 210. The windings 320a and 320a' are then deenergized, causing the portion of diaphragm portion 202 adjacent the inlet port 310 to move back to its rest position against valve plate 221, thereby closing the inlet valve 330. At the same time, windings 320c and 320c' are energized, causing the fluid trapped in the pump chamber to move into the region defined by the energized windings 320b, 320b' and 320c, 320c'.

The pump cycle continues in this fashion, with the windings energized in the sequence shown in the timing diagram of FIG. 15. The signal which energizes the respective windings 320d and 320d' is that represented by wave form D of FIG. 15. Similarly, windings 320e and 320e' are energized by a signal which is represented by wave form E. The signal which energizes the outlet valve 340 actuator windings 320f and 320f' is represented by wave form F.

It will be appreciated that variations in the signals used to energize the windings are possible. For example, it would be possible to increase the volume of fluid delivered by the pump by energizing more of the windings before the inlet valve is closed. This would have the effect of increasing the size (volume) of the pump chamber.

In the case where only very small changes in the lens power are required and the volume of fluid to be pumped is therefore small, the dimensions of the pump may be correspondingly reduced. The limited capacity of the smaller sizes may also be an advantage where very precise control of the lens power is desired.

In some applications it may be desirable to use the pump to maintain a precise fluid pressure in the adjustable lens. It is possible to incorporate a conventional semiconductor pressure transducer as a part of the control loop for the pump. Since such transducers are fabricated with the same semiconductor processing techniques as the pump, it is possible to incorporate such transducers in the same wafer or chip as the pump itself with the advantages of increased reliability and smaller size.

The various pumps have been described with actuators of the electromagnetic variety. The windings on the diaphragm and base member can be replaced with simple electrostatic plates and the plates simply charged with the appropriate voltages to cause the desired movement of the valves and diaphragm. The voltages required to operate an electrostatic actuator system will be higher than generally required for the electromagnetic version. While such voltages are not conveniently obtainable directly from batteries, they are easily obtained with conventional circuitry which can be fabricated directly on the same wafer or chip as the pump itself. The wave form of the electrostatic drive signals will be essentially the same as shown in FIG. 15.

In the case where corrosive fluids are to be pumped into the lens, it is possible to passivate the surfaces of the pump which come into contact with the fluid. An oxide coating will be adequate in most situations, but a coating of gold or similar material may sometimes be necessary.

The pump may be powered from conventional batteries since the consumption of power will be very low. Rechargable batteries can also be used since the circuitry for intercepting energy for recharging can be easily incorporated on the semiconductor wafer or chip used to fabricate the pump. In the case where the pump is positioned near the front surface of the eye, infrared or even visible light can be used for recharging. The light would be projected onto solar cells incorporated into the chip.

The use of an alterable storage unit on the semiconductor chip allows the control algorithm for the pump to be modified even after the pump is implanted. The use of a simple radio frequency detector and conventional radio frequency signalling techniques would allow the program to be altered to suit existing conditions. Alternatively, since the device is accessible to visible light, a simple optical device can be used to reprogram the device.

Various modifications can be made to the present invention without departing from the apparent scope thereof. The implanted switch can also be a receiver for receiving RF signals from an external source for energizing and providing communications command controls to the microprocessor control for regulating the distance between the two lenses.

I claim:

1. Intraocular lens system for implantation in an eye, comprising:
   a. implantable intraocular first lens means constructed of a substantially stiff material including means for supporting said lens means in an anterior chamber or a posterior chamber of said eye;
   b. second movable lens means constructed of a material of a soft and pliable nature secured to and disposed over said first lens means, said second lens means of a material for positioning of said second lens at a distance away from said first lens;
   c. means for moving said center of said second lens said distance away from said first lens, said movement means positioned in and about said first lens means, and connected to space between said first and second means;
   wherein said movement means comprises:
   (i) fluid reservoir means positioned about the circumference of said first leans means;
   (ii) pump means and valve means, said pump means being connected between said reservoir and said valve means; and,
   (iii) means for connecting said valve means to said space between said first and second lens means.

2. System of claim 1 wherein said first lens means is an anterior chamber lens.

3. System of claim 2 wherein said first lens means is of PMMA material.

4. System of claim 1 wherein said first lens means is a posterior chamber lens.

5. System of claim 4 wherein said first lens means is of PMMA material.

6. System of claim 1 wherein said second movable lens means is of pliable rubber and secured about an edge of said first lens means.

7. System of claim 6 wherein said pliable rubber is silicon rubber.

8. System of claim 6 wherein said pliable rubber is urethane.

9. System of claim 1 wherein said fluid is distilled water.

10. Intraocular lens system for implantation in an eye, comprising:
    a. intraocular first lens means including means constructed of a substantially stiff material for supporting said lens means in an anterior or posterior chamber of the eye;
    b. second movable lens means secured to a periphery of said first lens means and disposed over said first lens means, said second means of a material of a soft and pliable nature for positioning over said first lens means at a distance away from said first lens means;
    c. means for storing fluid in a perimeter reservoir about a circumferential edge of said first lens means; d. means situated within said first lens means for pumping fluid from said reservoir means to space between said first lens means and said second lens means, said pump means connected to said reservoir means, and valving means connected between said pump means and said space between said first lens means and second lens means; and,
    e. means for controlling said pump, said means including computer means for turning said pump on and off on an external command whereby said controlling means controls said pump means for pumping fluid from said fluid storage means for allowing for accommodation from distance to near vision of the focal point between said first lens means and said second lens means thereby fine tuning the focal point of a lens implanted into said eye.

11. System of claim 10 wherein said first lens means if of PMMA material.

12. System of claim 10 wherein said second lens means is of silicon material.

13. System of claim 10 wherein said controlling means is a RF signal external to the eye.

* * * * *